(12) United States Patent
Foster et al.

(10) Patent No.: US 7,384,645 B2
(45) Date of Patent: Jun. 10, 2008

(54) OUTER MEMBRANE VESICLES FROM GRAM NEGATIVE BACTERIA AND USE AS A VACCINE

(75) Inventors: Keith Alan Foster, Salisbury (GB); Andrew Richard Gorringe, Salisbury (GB); Michael John Hudson, Salisbury (GB); Karen Margaret Reddin, Salisbury (GB); Andrew Robinson, Salisbury (GB)

(73) Assignee: Health Protection Agency, Salisbury, Wiltshire (GB)

( * ) Notice: Subject to any disclaimer, the term of this patent is extended or adjusted under 35 U.S.C. 154(b) by 324 days.

(21) Appl. No.: 10/499,063

(22) PCT Filed: Dec. 17, 2002

(86) PCT No.: PCT/GB02/05718

§ 371 (c)(1),
(2), (4) Date: Jun. 17, 2004

(87) PCT Pub. No.: WO03/051379

PCT Pub. Date: Jun. 26, 2003

(65) Prior Publication Data

US 2005/0013831 A1    Jan. 20, 2005

(30) Foreign Application Priority Data

Dec. 17, 2001    (GB) ................. 0130123.3

(51) Int. Cl.
| A61K 39/095 | (2006.01) |
| A61K 39/116 | (2006.01) |
| A61K 39/02 | (2006.01) |
| A61K 39/00 | (2006.01) |
| A61K 38/00 | (2006.01) |
| C07K 1/00 | (2006.01) |

(52) U.S. Cl. ............... 424/250.1; 424/203.1; 424/234.1; 424/184.1; 424/249.1; 514/2; 530/350; 530/825

(58) Field of Classification Search ............ 424/234.1, 424/203.1, 184.1, 200.1, 250.1, 249.1; 514/2; 530/350, 825; 435/69.3, 71.1
See application file for complete search history.

(56) References Cited

U.S. PATENT DOCUMENTS

| 6,180,111 B1 | 1/2001 | Stein et al. | |
| 6,451,317 B1 * | 9/2002 | Blake et al. | 424/197.11 |
| 6,936,261 B2 * | 8/2005 | Granoff et al. | 424/249.1 |
| 7,081,244 B2 * | 7/2006 | Robinson et al. | 424/234.1 |
| 2003/0021812 A1 | 1/2003 | Robinson et al. | |
| 2003/0026809 A1 * | 2/2003 | Robinson et al. | 424/190.1 |
| 2003/0215469 A1 | 11/2003 | Robinson et al. | |

FOREIGN PATENT DOCUMENTS

| WO | WO 90/06696 A2 | 6/1990 |
| WO | WO 97/05899 A2 | 2/1997 |
| WO | WO 00/25811 A2 | 5/2000 |
| WO | WO 00/50074 A2 | 8/2000 |
| WO | WO 01/09350 A2 | 2/2001 |
| WO | WO 01/52885 A1 | 7/2001 |
| WO | WO 01/91788 A1 | 12/2001 |

OTHER PUBLICATIONS

Ferreiros et al. FEMS Microbiol. Lett. 83: 247-254, 1991.*
Griffis et al. Trans. Roy. Soc. Trop. Med. Hyg. 85: 32-36, 1991.*
United Kingdom Search Report for Great Britain Application No. 0130123.3, UK Paten Office, UK, mailed Aug. 19, 2002.
Bracegirdle, P., et al., "*Neisseria lactamica* Provides a Cross-reactive Vaccine Against Meningococcal Disease," *Program and Abstracts of the Interscience Conference on Antimicrobial Agents and Chemotherapy* 40:248, American Society for Microbiology (Sep. 2000).
Cartwright, K., et al., "Immunogenicity and reactogenicity in UK infants of a novel meningococcal vesicle vaccine containing multiple class 1 (PorA) outer membrane proteins," *Vaccine* 17:2612-2619, Elsevier Science Ltd. (1999).
International Search Report for International Patent Application No. PCT/GB02/05718, European Patent Office, Netherlands, mailed May 7, 2003.

* cited by examiner

*Primary Examiner*—S. Devi
(74) *Attorney, Agent, or Firm*—Sterne, Kessler, Goldstein & Fox P.L.L.C.

(57) ABSTRACT

A composition is prepared from a mixture of different vesicles, such as outer membrane vesicles (OMVs) and vaccines are based thereon. Another composition comprises in a single vesicle a combination of antigens and/or other vesicle components deriving from separate vesicles; again vaccines are prepared therefrom.

4 Claims, 3 Drawing Sheets

OUTER MEMBRANE VESICLES FROM GRAM NEGATIVE BACTERIA AND USE AS A VACCINE

BACKGROUND OF THE INVENTION

1. Field of the Invention

The present invention is in the field of compositions comprising vesicles, such as liposomes and outer membrane vesicles (OMVs) obtainable from Gram negative bacteria, methods of making such compositions and vaccines based thereon. In particular, the invention relates to vaccines and pharmaceutical compositions comprising OMVs obtained from *Neisseria* species.

2. Description of the Related Art

A significant number of human and animal pathogens fall within the Gram negative classification of bacteria, including members of the genus *Neisseia, Moraxella, Kingella, Acinetobacter, Brucella, Bordetella, Haemophilus, Escherichia, Chlamydia, Legionella, Pseudomonas, Proteus* and *Yersinia. Neisseria meningitidis* (the meningococcus) is the organism that causes meningococcal meningitis and is of particular importance as a worldwide health problem. In many countries the incidence of this disease is increasing. *N. meningitidis* is also responsible for meningococcal septicaemia, which is associated with rapid onset and high mortality, with around 22% of cases proving fatal. Other Gram negative bacteria are responsible for a range of human infections including meningitis (*H. influenzae*), plague (*Y. pestis*), gastroenteritis (*E. coli*), venereal disease (*N. gonorrhoeae*) and nosocomial infection (*P. aeruginosa*).

It would be desirable to provide alternative broad spectrum vaccines that provide protective immunity in animals, particularly humans, against Gram negative bacterial infection, and especially infection by Gram negative pathogens.

Many known vaccines are based upon preparations of capsular polysaccharide, however, these vaccines are often limited in their protective value. For example, vaccines directed at providing protective immunity against meningococcal disease provide only limited protection because the protection tends to be strain specific whereas there are many different strains of *N. meningitidis*. Vaccines based upon the serogroup antigens, the capsular polysaccharides, offer only short lived protection against infection and do not protect against many strains commonly found in North America and Europe. In fact, certain capsular polysaccharides, such as that from the group B meningococcal capsule, are essentially non-immunogenic in humans.

The outer membrane of many Gram negative bacteria is highly dynamic and can produce vesicles that bud off and are released into the surrounding environment. These outer membrane vesicles (OMVs), also referred to as blebs, comprise many of the outer membrane proteins (OMPs) and lipopolysaccharide (LPS) that contribute to the antigenic profile of the organism.

There have been a number of attempts to generate an OMV based vaccine in the hope that it could overcome the disadvantages seen in previous capsular polysaccharide based vaccines. In Bjune et al. (Lancet (1991) 338: pp 1093-1096) a vaccine consisting of OMVs from group B *N. meningitidis* is described (Norwegian vaccine). Bjune et al. show that the vaccine was able to induce a protective efficacy against meningococcal disease of 57.2% in a clinical trial in Norway. A similar vaccine has been produced in Cuba (Sierra et al., NIPH Ann (1991) December;14(2): pp 195-207) and high levels of efficacy were observed in that country. However, a large study in Brazil showed poor efficacy of the Cuban vaccine, especially in young children (de Moraes et al., Lancet (1992) October 31;340(8827): pp 1074-1078).

To address the difficulties associated with achieving broad spectrum protection researchers have attempted to "enrich" OMVs with particular antigens that might enhance the immunogenic potential of the OMV. In WO-A-00/25811 OMVs isolated from *N. meningitidis* are combined with heterologous antigens, e.g. Tbp, or a genetically modified *N. meningitidis* expresses such antigens recombinantly and antigen enriched OMVs are derived therefrom. A similar approach was adopted by researchers in WO-A-01/09350 which describes vaccine compositions comprising OMVs from *N. meningitidis, M. catarrhalis* and *H. influenzae*, where in certain embodiments these organisms have been genetically modified to overexpress particular immunogenic moieties.

A further OMV based vaccine composition is known as the Hexamen™ or Dutch vaccine (Cartwright et al., Vaccine 17 (1999), pp 2612-2619). The Hexamen™ vaccine composition comprises *N. meningitidis* OMVs that include six different PorA proteins that are recombinantly produced using two vaccine strains of *N. meningitidis*, PL16215 and PL10124. Each strain is capsule negative and produces three different PorA proteins, CPS$^-$P1.7,16;P1.5,2; P1.19,15 and CPS$^-$P1.5$^c$,10; P1.12,13; P1.7$^h$,4 respectively.

Ruppe Van der Voort et al (Vaccine (2000) 18(14); pp 1334-1343) show that the hexamen vaccine induces specific serum bactericidal antibodies against all six PorA serosubtypes included in the vaccine. However, the Hexamen™ vaccine suffers from certain drawbacks. It is not currently possible to express all six PorA proteins in a single *N. meningitidis* cell due to host toxicity problems. Hence, three PorAs are expressed in one cell and three in another. OMVs from cell cultures each expressing three PorAs are obtained and then admixed to give the hexavalent vaccine.

PorA is an immunodominant antigen, meaning that it masks most other antigens presented on the OMV surface—i.e. Hexamen™ vaccine is heavily biased towards PorA as the protective antigen. This, in turn, leads to selection pressure in the population towards strains of *N. meningitidis* that express PorAs that are antigenically different to those in the Hexamen™ vaccine. There is, therefore, a risk that strains of *N. meningitidis* that are not protected against by the Hexamen™ vaccine will predominate in time, resulting in ongoing efforts to continually modify the vaccine to protect against strains currently infecting and causing disease in the human population.

It would be desirable to provide an OMV vaccine composition that provides broad spectrum protection to infection from a number of bacterial species and at least a wide range of strains within a single bacterial genus. It would be particularly desirable to produce an OMV-based vaccine that provides broad spectrum, long term protection against disease caused by a range of strains of Gram negative bacteria, and especially *N. meningitidis*.

It would further be desirable to provide further and/or improved methods of preparing vesicle-containing compositions.

SUMMARY OF THE INVENTION

Accordingly, the present invention provides methods and compositions comprising vesicles, especially OMVs, and vaccine compositions based thereon which can provide a broad scope of protection to infection from Gram negative bacterial pathogens, such as *N. meningitidis*.

An advantage of compositions and vaccines of the present invention is that the OMVs are derived from a diversity of Gram negative bacterial sources, thus allowing the composition to present a broad spectrum of antigens to the host immune system, and thereby generating broad spectrum protective immunity.

The present invention also provides methods of combining vesicles, especially OMVs, vesicles obtained thereby and vaccine compositions based thereon. Advantages of the combining include control of vesicle content and/or facilitation of antigen combinations in the resultant vesicles.

DETAILED DESCRIPTION OF THE INVENTION

In order to facilitate understanding of the present invention a number of terms used herein are defined in more detail below.

Gram negative bacteria are those bacteria that fail to resist decolourisation in the commonly known Gram staining method. Gram negative bacteria are characterised by a complex multilayer cell wall and often possess an outer layer polysaccharide capsule—e.g. *N. meningitidis*, although in some species this capsule is absent—e.g. *N. lactamica*.

The term "pathogenic" as used herein refers to an organism that is capable of causing disease, particularly in animals and especially in humans.

The term "non-pathogenic" refers to organisms that do not cause disease in animals, in particular in humans. The term includes commensal organisms. Commensal organisms are those that can colonize a host organism without signs of disease. Examples of commensal organisms include the commensal *Neisseria* species, such as *N. lactamica, N. sicca, N. cinerea, N. perflava, N. subflava, N. elongata, N. flavescens*, and *N. polysaccharea*.

Outer membrane vesicles (OMVs), also referred to as blebs, are vesicles formed or derived from fragments of the outer membrane of a Gram negative bacterium. OMVs typically comprise outer membrane proteins (OMPs), lipids, phospholipids, periplasmic material and lipopolysaccharide (LPS). Gram negative bacteria, especially pathogens like *N. meningitidis*, often shed OMVs during virulent infections in a process known as blebbing. OMVs can also be obtained from Gram negative bacteria via a number of chemical denaturation processes described in more detail in the Examples below. Liposomes, comprising a lipid bilayer and typically enclosing an aqueous core, can be regarded for the purposes of the present invention as constituting a synthetic equivalent to OMVs, and embodiments of the invention described with reference to OMVs apply mutatis mutandis to embodiments carried out with and relating to liposomes. A distinction between liposomes and OMVs may be made for example in embodiments in which control of content of a liposome is possible whereas OMV content is not so readily controllable.

A "vaccine" as referred to herein is defined as a pharmaceutical or therapeutic composition used to inoculate an animal in order to immunize the animal against infection by an organism, typically a pathogenic organism. A vaccine will typically comprise one or more antigens derived from one or more organisms which on administration to an animal will stimulate active immunity and protect that animal against infection with these or related pathogenic organisms.

Vaccine compositions that are formulated as pharmaceuticals will typically comprise a carrier. If in solution or in liquid aerosol suspension, suitable carriers can include saline solution, sucrose solution, or other pharmaceutically acceptable buffer solutions. An aerosol formulation will typically additionally comprise a surfactant. Alternative vaccine compositions include microencapsulated OMV compositions. Such microcapsules with generally comprise a biocompatible polymer shell or core, such as made from polylactide-co-glycolide (PLG). Vaccine compositions can additionally comprise an adjuvant, for example where administration is via the parenteral route. Suitable adjuvants include aluminium hydroxide.

Vaccines are suitably administered to an animal via a number routes. For example, parenterally—e.g intramuscularly, trans-dermally—or via other routes—e.g. intra-nasally, orally, topically—or via any other commonly known administrative route.

Certain proteins can be recombinantly expressed in Gram negative bacteria and thereby enable enrichment or alteration of the antigenic profile of the bacterial outer membrane. Genetic modification of a bacterial source organism thereby allows for manipulation of the antigenic profile of OMVs that are obtained from these organisms. When proteins that are not normally present in the bacterial outer membrane, and thus in an OMV derived therefrom, are introduced via recombinant expression techniques, these "non-native" proteins and polypeptides are described as heterologous antigens. The contents of WO-A-00/25811 and WO-A-01/09350 are incorporated herein. Thus it is an advantage of the invention that the vaccine comprises OMVs rather than live attenuated or dead pathogenic organisms which can pose a greater risk of infection or toxicity.

A first aspect of the invention mixes different vesicle preparations. This may be done to alter the immunogenicity of a first OMV preparation or to mix useful properties in respective preparations.

The invention thereby provides compositions comprising vesicles derived from two or more sources. The vesicles are preferably lipid vesicles comprising a lipid bilayer surrounding an aqueous core. Typically the lipid vesicles are of unilamellar structure (i.e. a single lipid bilayer surrounds the aqueous core), although multilammellar lipid vesicles are also suitably used in the compositions of the invention.

These lipid vesicles are preferably synthetic vesicles such as liposomes or obtained from bacteria such as outer membrane vesicles (OMVs) by extraction of naturally occurring OMVs (N-OMVs) or using a detergent extraction (D-OMVs). They typically have sizes in the nanomolar to micromolar range, e.g. from 1 nm to 100 µM, more typically from 10 nm to 10 µm and preferably from 30 nm to 1 µm. Antigenic components can be located in any or all of the three main compartments of the lipid vesicle, namely:

1. attached to the either the interior or exterior surface of the lipid vesicle, for example via a membrane anchor domain, or attachment to a lipid moiety;
2. inserted into the lipid bilayer, for example where the antigenic component is itself a hydrophobic or lipid based entity; or
3. located within the aqueous center/core of the lipid vesicle.

Where liposomes are utilised in the compositions and methods of the invention these can typically contain a number of different lipids and fatty acids. Suitable lipids for inclusion in liposomes of the invention include but are not limited to phosphatidylinositol-(4,5)-diphosphate, phosphatidylserine, phosphatidylcholine, phosphatidylethanolamine, phosphatidylglycerol, cholesterol, beta-oleolyl-gamma-palmitoyl, certain lipopolysaccharides and galactocebrosides. Liposomes can be obtained commercially from a number of sources and methods for preparing liposomes suitable for use in the invention are known in the art.

The lipid vesicles for use in the invention can be enriched and/or supplemented with preferred antigenic components. Regimes for supplementing the lipid vesicles, whether they be liposomes or OMVs, include via direct combination in vitro where an energetic combination step can optionally be applied to facilitate integration of the antigenic component into one or more of the three aforementioned lipid vesicle compartments. Preferred, energetic combination methods include homogenisation, ultrasonication, extrusion and combinations thereof.

One advantage associated with liposomes is that the exact antigenic composition of the lipid vesicle can be controlled and batch to batch quality control maintained more easily than with lipid vesicles derived from biological sources. In addition, the physical properties of the liposome, such as size, are more easily controlled by modifying the lipid composition of the bilayer.

However, certain antigenic components are difficult to synthesise in vitro, or to isolate in pure form from biological sources. Further, certain antigenic components are difficult to integrate in antigenically active form into synthetic liposomes. Hence, in such cases OMVs are the preferred lipid vesicle. Further advantages of using OMVs are that antigenic components can be synthesised in the host organism from which the OMV is obtained thereby providing a convenient method for integrating a preferred antigenic component into a lipid vesicle.

In situations where a particular component is not desired in a lipid vesicle of the invention, for example endotoxin, different options apply when using liposomes or OMVs. It is apparent that as the composition of the liposome is synthetically controlled the non-desired component is simply not added to the liposome. This represents a further advantage associated with the use of liposomes. Where OMVs are preferred as the lipid vesicle, the OMVs can be obtained from organisms that are naturally free or low in the non-desired component, for example commensal organisms. Alternatively, knock out organisms can be generated where genes coding for or regulating the production of the non-desired component are deleted or silenced.

The lipid vesicles for use in the invention can also comprise a biologically active component, other than an antigen, within the aqueous center/core. This component is suitably selected from soluble adjuvants, cytokines, immunomodulatory agents, pharmaceuticals, excipients, proteins, polypeptides and pharmacologically or pharmaceutically active agents.

The invention also provides a composition comprising OMVs obtained from at least two different species of Gram negative bacteria, wherein at least one of said species is a non-pathogenic species. In general, all such bacteria are believed suitable, though Gram negative species especially suitable for use in the invention include those selected from *Neisseria, Moraxella, Kingella, Acinetobacter, Brucella, Bordetella, Porphyromonas, Actinobacillus, Borelia, Seffatia, Campylobacter, Helicobacter, Haemophilus, Escherichia, Legionella, Salmonella, Pseudomonas* and *Yersinia*. In a particular embodiment of the invention the composition comprises a pathogenic species is selected from strains of *N. meningitidis*.

The non-pathogenic species can suitably be any non-pathogenic Gram negative species. In a specific embodiment of the invention described in more detail below, the composition comprises OMVs obtained from a commensal *Neisseria*.

Compositions of the invention need not be limited to comprising OMVs from only two sources. The invention also provides compositions comprising OMVs from a plurality of Gram negative bacterial sources, from as few as three sources up to many tens or more. It is feasible for a library of a multiplicity of OMVs to be constructed and hence certain combinations of OMVs can be formulated into compositions, according to precise requirements, so as to provide a particular predetermined spectrum of vaccination coverage. For example, where a certain strain of pathogen is prevalent in a particular geographical area, OMVs specific to this pathogen are incorporated into a broad spectrum vaccine composition in order to provide improved local efficacy.

Combining a plurality of OMVs in a single vaccine composition provides a composition capable of conferring broad spectrum immunity and also enables the "dilution" of immunodominant antigens, such as PorA, which would otherwise mask the other antigens present in the composition.

Another composition of the invention comprises OMVs, which OMVs are obtained from a first and at least a second different species of *Neisseria*, wherein:
  1. the first species is a pathogenic species of *Neisseria*; and
  2. the at least a second species is a commensal species of *Neisseria*.

In a specific embodiment of the invention, the composition comprises OMVs obtained from a first and at least a second different species of *Neisseria*, wherein:
  1. the first species is selected from the group comprising *N. meningitidis* and *N. gonorrhoeae*; and
  2. the at least a second species is selected from the group comprising *N. lactamica, N. sicca, N. cinerea, N. perflava, N. subflava, N. elongata, N. flavescens,* and *N. polysaccharea*.

In a further specific embodiment of the invention, some or all of the OMVs in the composition also comprise a heterologous antigen. Suitable heterologous antigens include cell membrane associated proteins, or periplasmic proteins, such as PorA; Cu—Zn-SOD; TspA, LbpA, LbpB, pilQ, TbpA; TbpB and/or NspA. These can also be non-neisserial, such as *B. pertussis* toxin, diphtheria toxin, tetanus toxin, measles antigen, HIV antigens, smallpox antigen, and/or anthrax antigen. It should be noted that the OMVs of the invention provide advantageous presentation of antigens to the host immune system, thereby enabling broad spectrum, long term protective immunity.

A third composition of the invention is one comprising OMVs, which OMVs are obtained from a first neisserial source and at least a second neisserial source different from the first. The term "source" is used to refer to the genus and/or strain of *Neisseria* from which the OMVs are obtained or isolated. Hence, if OMVs are extracted from *N. meningitidis* strain K454, this is the neisserial source of the OMVs.

In one embodiment of the invention the first neisserial source is a commensal *Neisseria* and said at least second neisserial source is a pathogenic *Neisseria*. Alternatively, the first neisserial source can be a commensal *Neisseria* and said at least second neisserial source is also a commensal *Neisseria* but of a different species or strain to the first. For example, the first source is suitably *N. lactamica* and the second *N. cinerea*. In a second example, the first source is *N. lactamica* strain Y921009 and the second source is *N.*

*lactamica* strain 2086. A further option is to utilise different genetic mutants of the same strain.

As mentioned previously, the invention also utilizes OMV compositions derived from neisserial sources which are genetically modified so as to recombinantly express one or more heterologous antigens. This can be achieved by transforming the cells with an expression vector that comprises DNA encoding the desired antigenic polypeptide. Alternatively, an endogenous polypeptide can be upregulated or modified in some way as to be expressed either on the surface or within the periplasm of the cell, and thereby incorporated into OMVs extracted from that cell. Although such proteins are endogenous to the cell, their presence at abnormal levels in OMVs, can still be considered to fall within the scope of the term "heterologous antigen".

In a particular embodiment of the invention a first neisserial source is a commensal *Neisseria* that expresses a first heterologous antigen and the second neisserial source is a *Neisseria* that expresses a second heterologous antigen different from the first antigen. In a further embodiment of the invention a first neisserial source is a commensal *Neisseria* that expresses a first heterologous antigen and the least a second neisserial source is a commensal *Neisseria* of the same or a similar strain that expresses a second heterologous antigen different from the first antigen. Each source can further optionally express multiple heterologous antigens.

A fourth composition of the invention comprises an OMV containing outer membrane protein (OMP) and/or lipopolysaccharide (LPS) derived from at least two different species of Gram negative bacteria, such as *Neisseria*. In specific embodiments of the invention, the OMV is suitably derived from two species of *Neisseria* which include a commensal *Neisseria* and a pathogenic *Neisseria*, from at least two species of commensal *Neisseria*, or even from two different strains of the same commensal species. The OMV can optionally further comprise one or more recombinantly expressed polypeptides.

It is an advantage of the present invention that the OMVs derived from commensals typically have LPS of lower toxicity than the LPS found in the outer membrane of pathogenic species. Hence, vaccine compositions comprising commensal OMVs typically elicit lesser adverse reactions than compositions comprising pathogenic OMVs.

The LPS content of the OMV, however, also provides an adjuvant effect which itself enhances an immune response especially in compositions that are administered intra-nasally. It is a further option to derive OMVs from LPS null mutant or LPS modified species of Gram negative bacteria, suitably in cases where potential LPS toxicity is likely to cause extreme allergic reactions.

OMVs of the invention can be suitably mixed from sources such as Gram negative bacteria of different species or strains. Alternatively, OMVs can optionally be obtained from sources that are from the same commensal strain but where each source expresses different heterologous antigens. A further example of different OMVs from same strain sources is where OMVs are obtained from a Gram negative bacterial source at different phases in the organism's growth cycle. The OMVs are then combined into a single composition that represents the surface antigenicity profile of the organism throughout its growth cycle.

A second aspect of the invention combines different vesicle preparations so as to transfer a component of one vesicle, or one type of vesicle, to another. By way of example, liposomes are combined with liposomes, liposomes with OMVs and OMVs with OMVs.

The invention thus provides a method of preparing a composition, comprising:
1. obtaining a first composition which contains first vesicles, said first vesicles having a first antigenic component;
2. obtaining a second composition which contains second vesicles, said second vesicles having a second antigenic component different from the first antigenic component; and
3. combining the first and second compositions so as to obtain a third vesicles-containing composition, wherein the third vesicles-containing composition comprises third vesicles having both the first antigenic component and the second antigenic component.

A further method of the second aspect, for preparing lipid vesicles, comprises:
a. synthesising liposomes comprising a first antigenic component;
b. obtaining OMVs from an organism, said OMVs comprising a second antigenic component; and
c. mixing the liposomes of (a) with the OMVs of (b) so as to form a vesicle comprising both the first and the second antigenic component.

A still further method of the second aspect, for preparing an OMV containing composition, comprises:
1. isolating OMVs from a first species of Gram negative bacteria, wherein said first species is either pathogenic or non-pathogenic to humans;
2. isolating OMVs from at least a second species of Gram negative bacteria different from the first, wherein said second species is non-pathogenic to humans;
3. combining the OMVs from (1) and (2) to form a hybrid OMV containing at least a portion of an OMV from step 1 and at least a portion of an OMV from step 2.

The second aspect of the invention extends also to compositions obtainable and obtained using the above methods, to pharmaceutical compositions, to methods of medical treatment as herein described, to uses as herein described, all based thereon.

In use of methods of this aspect of the invention, the combining of the two separate compositions, containing distinct vesicles, is carried out so as to effect a transfer of an antigen between the respective compositions, resulting in production of a third type of vesicle which contains antigenic components derived from both the first and the second original vesicles. An advantage of this combination is that there is provided as a result a vesicle containing both first and second antigenic components, and this can be purified so as to provide a homogenous preparation of vesicles containing both such antigenic components.

This means of providing a vesicle with both antigenic components can be easier than, for example, carrying out a transfection of a bacteria so that it expresses both antigenic components. In addition, as can be appreciated, homogenous preparation of many different combinations of antigens can be prepared from starting materials comprising individual vesicles containing individual antigenic components of interest. Different antigens may be expressed at different levels in the same bacterial host. Using the above methods of combination of vesicles, by control of the starting amount/concentration of each respective vesicle, with its respective antigen, the relative amounts/concentrations of antigens in the final resultant combined vesicle can be controlled.

It is preferred to separate the third vesicles from the third-vesicles-containing composition, to obtain a purified preparation of the third vesicles. This can be carried out using a double-immune method. Thus, a first purification is carried out with an antibody (e.g. immobilized), specific for the first antigen; a second purification is then carried out using an antibody specific for the second antigen—this purifies the composition in respect of vesicles containing both antigens.

Both OMVs and liposomes, and combinations thereof are suitable for the methods of the second aspect, with OMVs preferably being derived from Gram negative bacteria as previously described—though especially from *Neisseria*.

In a development of the second aspect of the invention, a liposome containing a component other than (or in addition to) an antigen can be combined with an antigen-containing vesicle.

Thus, one such method of preparing a composition, comprises:
1. obtaining a first composition which contains first vesicles, said vesicles having an antigenic component;
2. obtaining a second composition which contains second vesicles, said second vesicles comprising a soluble, biologically active component within aqueous cores of the vesicles; and
3. combining the first and second compositions so as to obtain a third vesicles-containing composition, wherein the third vesicles-containing composition comprises third vesicles which both comprise the antigenic component and also contain, within an aqueous core, the soluble, biologically active component.

These resultant vesicles confer the advantage of combining, at the control of the user, the antigen from one source and the liposome contents of another, resulting in provision of further methods for preparation of vesicles for vaccination and other uses.

In a preferred composition of the invention liposomes comprising one or more antigenic components are combined with OMVs in a single composition. Following a fusion event in which a modified energetic combination step is employed, resulting hybrid or chimaeric lipid vesicles are formed.

In a further preferred composition of the invention liposomes comprising one or more antigenic components are combined with OMVs in a single composition so that antigens from OMVs are exchanged or transferred to liposomes and vice versa. After the antigen exchange step, the liposomes and OMVs can be separated (for example, by centrifugation) and form distinct compositions in their own right for application as vaccine compositions as described further herein.

A further aspect of the invention provides an OMV composition, characterised in that each OMV in said composition comprises OMP and LPS from at least two different species of *Neisseria*. Optionally, at least one of the species of *Neisseria* is a commensal *Neisseria*. It is further optional for one of the species to be a pathogenic species of *Neisseria*, for example *N. meningitidis* or *N. gonorrhoeae*.

In further examples of the invention, there are provided methods of preparing an OMV composition comprising the steps of:
1. obtaining OMVs from a first species of Gram negative bacteria, wherein said first species is either pathogenic or non-pathogenic to humans;
2. obtaining OMVs from at least a second species of Gram negative bacteria different from the first, wherein said second species is non-pathogenic to humans; and
3. combining the OMVs from (1) and (2).

Also provided is a method for preparing a vaccine composition, which method is substantially identical to the above-mentioned method, but which instead comprises the step of:
3. combining the OMVs from (1) and (2) together with a pharmaceutically acceptable carrier.

Suitable methods for extracting OMVs from bacterial sources include deoxycholate extraction, Tris/HCl/EDTA extraction, and lithium acetate extraction. Protocols for performing such extractions are described in more detail in the Examples below. However, it will be appreciated by the skilled person that virtually any chemical and/or physical technique that enables disruption of the bacterial cell outer membrane in order to release sufficient OMVs for purification and isolation, would be suitable for preparation of the compositions of the invention In a specific embodiment of the invention, combined OMVs are homogenised in a low power homogeniser (e.g. Waring blender or Silverson homogeniser or by ultrasonication). This additional step has the effect of disrupting the OMVs in the mixture such that they fuse to form hybrid OMVs. In this way a single OMV can comprise OMPs, LPS and heterologous antigens from a plurality of bacterial sources. The fused chimaeric OMVs advantageously enable the presentation of multiple antigens to a host immune system in a uniquely immuno-available form.

Further aspects of the invention provide methods of vaccinating animals, especially humans, against Gram negative bacterial infection utilising the compositions of the invention. In particular, the invention provides methods for vaccinating animals against meningococcal infection. Also provided are uses of the compositions of the invention in the vaccination of animals, including humans, against Gram negative bacterial infection. Further provided are uses of the compositions of the invention in the manufacture of vaccines for inoculating animals in order to stimulate protective immunity to Gram negative bacterial infection. OMVs are of use in mucosally administered compositions, as LPS toxicity is less and LPS can function as an adjuvant.

The invention is now described in specific examples with reference to the accompanying drawings in which.

EXAMPLES

Example 1

Deoxycholate Extraction to Produce OMVs

This method is based on that used to produce the Norwegian Institute of Public Health OMV vaccine for parenteral delivery (Fredriksen, J H et al. (1991) Production and characterisation of menB-vaccine "Folkehelsa": an outer membrane vesicle vaccine against group B meningococcal disease. NIPH Annals 14 (2): 67B 80).

Reagents

Frantz medium

Buffer 1: 0.1M Tris-HCl pH8.6 containing 10 mM EDTA, 0.5% (w/v) deoxycholate (DOC), 0.01% (w/v) thiomersal.

Buffer 2: 50 mM Tris-HCl pH8.6 containing 2 mM EDTA, 1.2% (w/v) DOC, 20% (w/v) sucrose, 0.01% (w/v) thiomersal Buffer 3: 50 mM Tris-HCl pH8.6 containing 3% (w/v) sucrose, 0.01% (w/v) thiomersal Method
1. Appropriate *N. meningitidis* or commensal *Neisseria* strains were grown in Frantz medium at 37° C. with shaking until cultures had reached early stationary phase.
2. Once cultures reached early stationary phase the culture was stored overnight at 4-8° C.
3. The culture was harvested by centrifugation, 5000×g for 15 min at 4° C.
4. To the pellet, buffer 1 was added using a ratio of buffer to biomass of 5: 1 (v/w).
5. The suspension was centrifuged at 20,000×g for 30 min at 4° C. and the supernatant retained.
6. The extraction was repeated with 0.1M Tris buffer with the volume reduced to one third of that used in step 4. Again, the supernatant was retained.
7. The supernatant from steps 5 and 6 was pooled and ultracentrifuged at 100,000×g for 2 h at 4° C.
8. The resultant OMV pellet was resuspended in buffer 2.
9. Ultracentrifugation was repeated as in step 7.
10. OMVs were then homogenised in buffer 3.
11. OMV preparation was stored at 4-8° C.

Example 2

Tris-HCl/EDTA Extraction to Produce NOMVs (Native OMVs)

This method is based on that used by N. B. Saunders et al. (Immunogenicity of intranasally Administered Meningococcal Native Outer Membrane Vesicles in Mice. Infection and Immunity (1999) 67 (1): p.113-119). OMVs prepared in this way have been used as an intra-nasal vaccine in human volunteers.

Reagent
Stock NOMV buffer: 0.15M NaCl, 0.05M Tris-HCl, 0.01M EDTA pH 7.5.

Method
1. The culture (Fe limited) was prepared in 500 ml Frantz medium per strain.
2. Cells from the 500 ml culture in step 1 were centrifuged at 3500 rpm for 15 minutes.
3. Cells were resuspended in 25 ml NOMV buffer.
4. The suspension was warmed at 56° C. for 30 minutes.
5. The suspension was sheared in Waring blender for 3 minutes (low speed).
6. The suspension was centrifuged at 23,500 g for 20 minutes.
7. The supernatant was retained.
8. The pellet was resuspended in 12 ml distilled water and centrifuged at 23,500 g for 20 minutes.
9. The supernatant was retained and combined with supernatant from step 7.
10. The supernatants were centrifuged at 23,500 g for 20 minutes.
11. The supernatant was retained and centrifuged at 100,000 g for 2 hours
12. The pellet was washed by repelleting from distilled water.
13. Resulting NOMVs were stored in PBS at 4° C.

Example 3

Lithium Acetate Extraction to Produce OMVs

This is a further alternative method of producing OMVs (Hamel, J. et al. 1987. J. Med. Microbiol. 23,163-170).

Reagent
Lithium acetate buffer:–200 mM Lithium acetate+5 mM EDTA pH 6.0

Method
1. The broth culture (Fe limited) was prepared in 100 ml MHB per strain.
2. Cells from 100 ml culture were centrifuged at 3500 rpm for 15 minutes.
3. Cells were resuspended in 20 ml Lithium acetate buffer (LiAc)(for 750 ml cultures, resuspend cell pellet in 30 ml LiAc)
4. The suspension was incubated for 3 h at 37° C. with shaking (180 rpm).
5. The cell suspension was then passed through a 21 gauge needle 7 times, alternatively a bead beater can be used.
6. The suspension was centrifuged at 16000 rpm for 20 minutes.
7. The supernatant was carefully recovered.
8. The supernatant was centrifuged at 35,000 rpm for 2 h and the pellet collected.
9. The pellet was resuspended in PBS and stored at 4° C.

Example 4

Alternative Deoxycholate Extraction Method for Production of an OMV Based Vaccine Suitable for Parenteral Administration
1. Strains were cultured in Frantz medium (135 l) to early stationary phase; cells were harvested by continuous flow centrifugation and resuspended in NaCl buffer.
2. The cell suspension was homogenised for 30 min and the total wet weight of the suspension determined.
3. The cell suspension was centrifuged for 60 min at 2900×g and the pellet resuspended in 0.1M Tris-10 mM EDTA buffer at a ratio of 7.5:1 wet weight
4. Extraction of the vesicles was performed by the addition of $\frac{1}{20}^{th}$ volume of 0.1M Tris, 10 mM EDTA, 10% deoxycholate (DOC).
5. Vesicles were separated from cell debris at 20000×g at 4° C. for 1 h
6. The supernatant containing the vesicles was concentrated by ultracentrifugation at 125000×g at 4° C. for 2h.
7. The OMV pellet was resuspended in 0.1M Tris, 10 Mm EDTA, 0.5% DOC buffer and the suspension centrifuged again at 125000×g at 4° C. for 2 h.
8. The concentrated OMVs were resuspended in 3% sucrose solution
9. To prepare the adjuvanted vaccine, OMV extracts were mixed in equimolar amounts with $AlPO_4$ as adjuvant.

Example 5

Blended OMV Vaccine Composition

Separate OMV extracts prepared according to any of the methods described in Examples 14 are obtained from *N. meningitidis* and *N. lactamica*. The OMV extracts are combined as per step 9 in Example 4.

Example 6

Blended OMV Vaccine Composition

*N. meningitidis* and *N. lactamica* cultures are mixed together prior to performing the OMV extraction methods described in Examples 1-4. Concentrated OMVs are resuspended in 3% sucrose solution.

Example 7

Blended OMV Composition

OMV extracts are obtained from *N. meningitidis* and *N. lactamica* according to any of the methods given in Examples 1-4. Extracts of each are combined into a single composition and then homogenized. Concentrated OMVs are resuspended in 3% sucrose solution.

Example 8

Blended OMVs Composition

Reagents
*N. lactamica* OMVs from strain Y92 1009
*N. meningitidis* OMVs from strain MC 58 (B:15:P1.7,16)
Anti-meningococcal serosubtype (PorA) P1.7 monoclonal antibody (95/706 from NIBSC, UK)
AffiniPure anti-mouse IgG (Jackson Immuno Research Laboratories) 6 nm colloidal gold conjugate
Blocking buffer (2% bovine serum albumin in PBS)
Conjugate buffer (0.02% Tween® 20, 0.1% BSA, 5% newborn calf serum in PBS)
1% potassium phosphotungstate (PTA) stain Method

*N. lactamica* (NL) and *N. meningitidis* (NM) OMVs were removed from storage at −20° C. and allowed to thaw at room temperature. A mixture of OMVs was prepared separately by adding equal volumes of NL and NM OMVs to a glass container and agitating gently using a pipette; all OMVs were then stored at 4° C. until required.

NM, NL and the mixture of OMVs were placed on 3 separate carbon coated copper grids and allowed to dry. The grids were then placed in 100 µl of a 1:500 dilution of meningococcal PorA monoclonal antibody and incubated at room temperature for 2 h. The grids were washed twice in blocking buffer (PBS containing 2% BSA) and added to a 1:20 dilution of 6 nm colloidal gold particles conjugated to AffiniPure anti-mouse IgG (Jackson Immuno Research Laboratories) in 0.02% Tween® 20, 0.1% BSA, 5% newborn calf serum in PBS.

Following 1 h incubation at room temperature the grids were washed twice in blocking buffer, once in distilled water and stained with 1% potassium phosphotungstate (PTA) for 5-10 sec. Grids were then examined by electron microscopy and are shown in FIG. 1-3.

Figure 1:
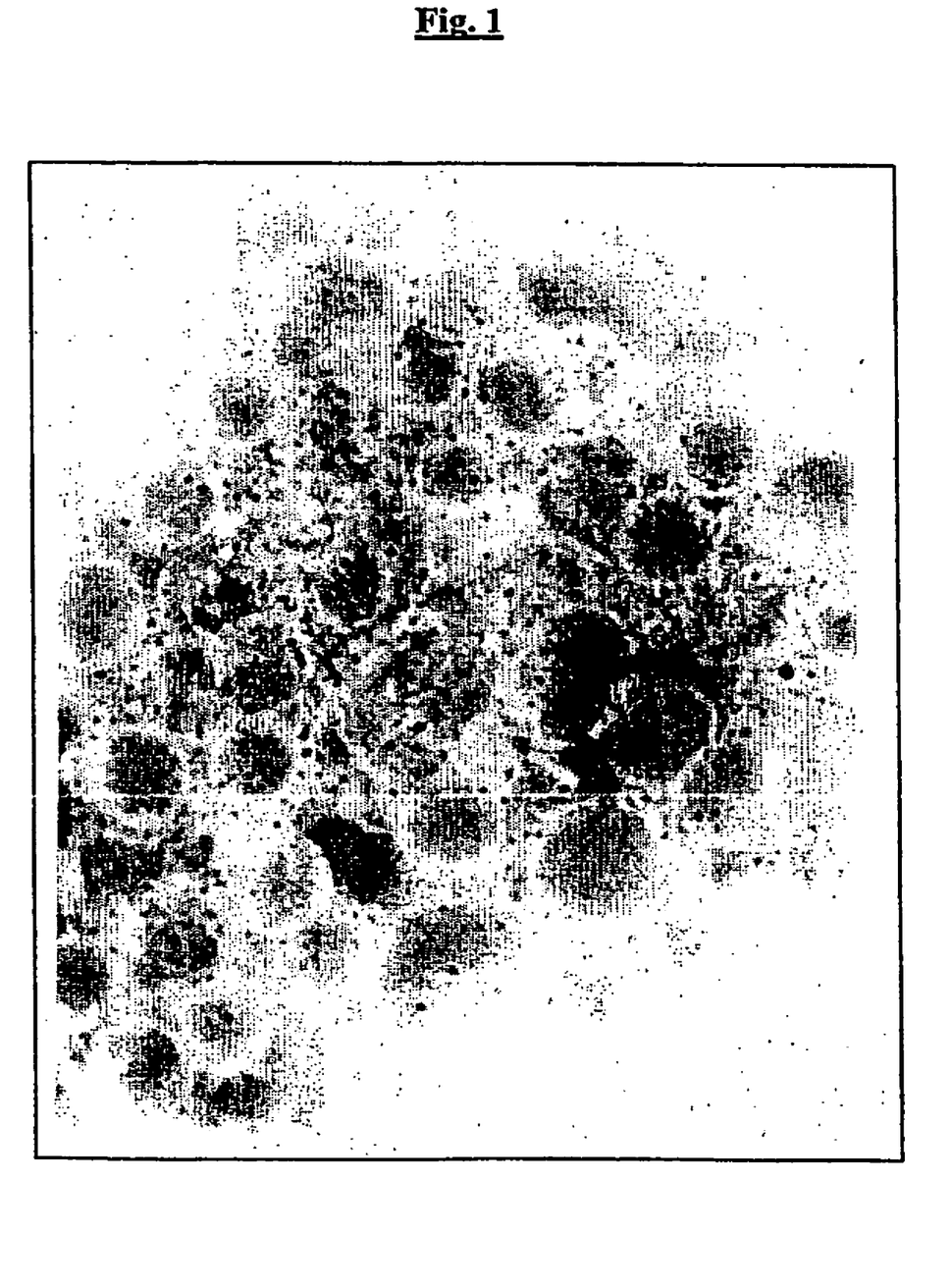
FIG. 1 shows an electron micrograph of a preparation of *N. meningitidis* OMVs.
Figure 2:
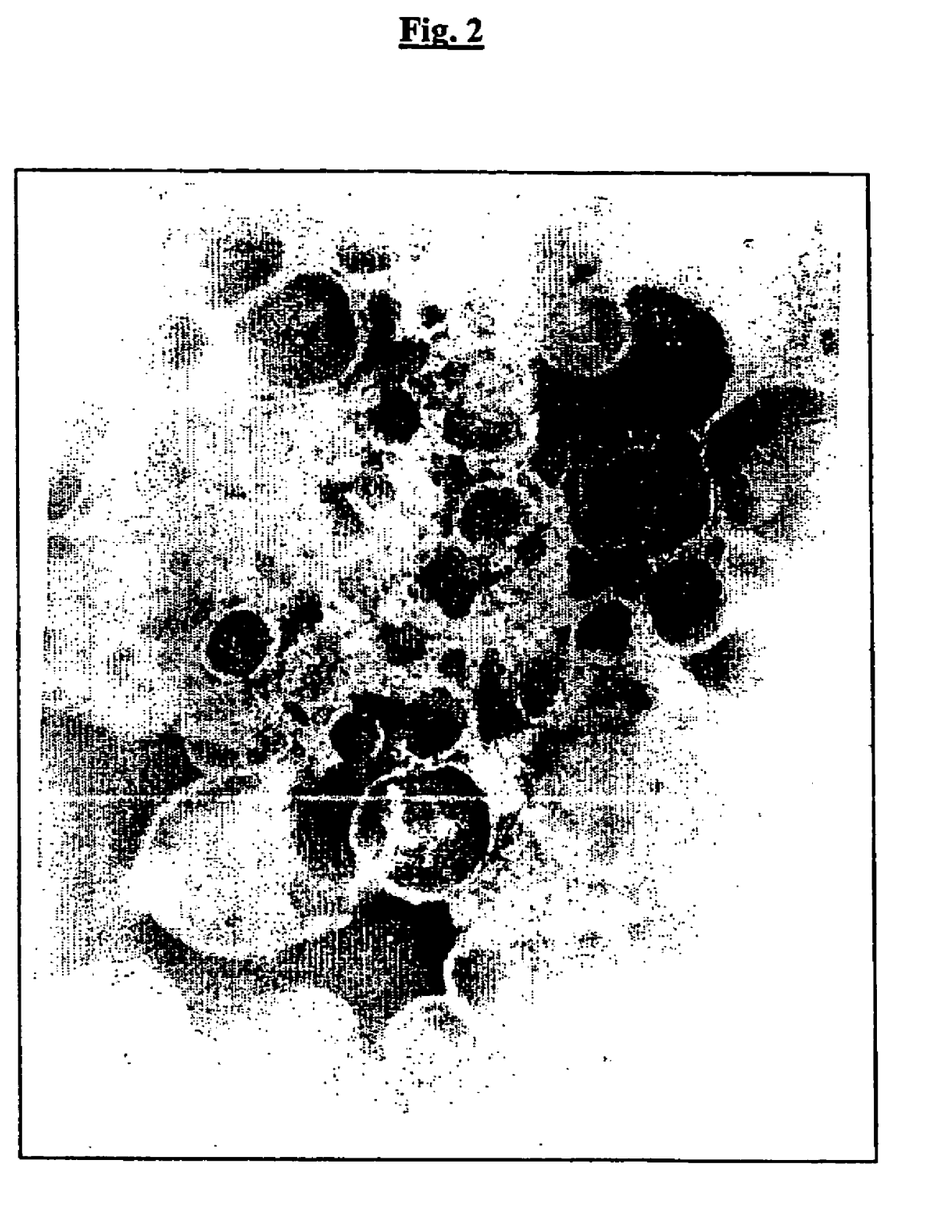
FIG. 2 shows an electron micrograph of a preparation of *N. lactamica* OMVs.
Figure 3:
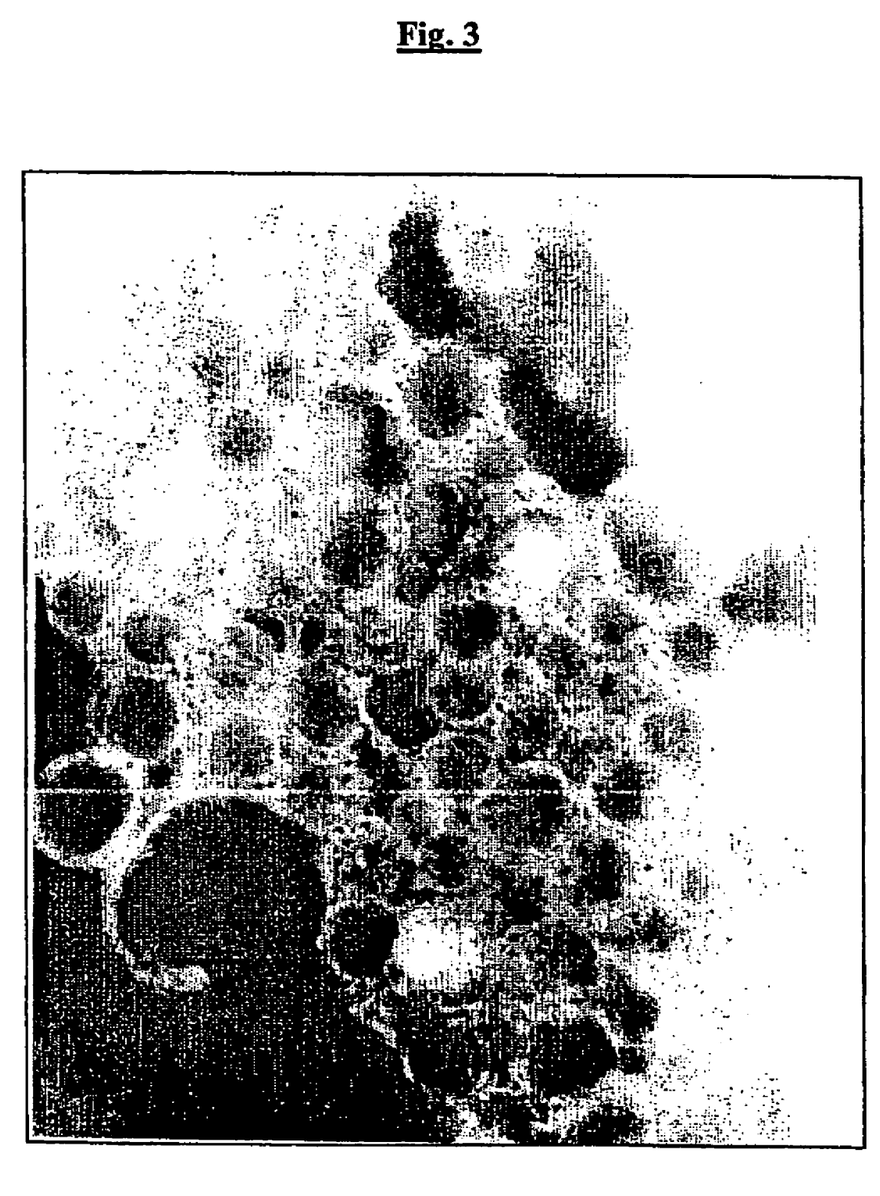
FIG. 3 shows an electron micrograph of a blend of *N. meningitidis* and *N. lactamica* OMVs according to the invention.

Black dots indicate labeling with the 6 nm gold particles in FIGS. 1, 2 and 3. In FIG. 1, NM OMVs are evenly labeled with the 6 nm gold particles, showing that PorA is present on all OMVs. In FIG. 2, there is no labeling, consistent with the fact that NL OMVs do not contain PorA (a pathogen—specific antigen not seen in commensal *Neisseria*). The FIG. 3 result, showing the combination of NM and NL OMVs, shows OMVs again evenly labeled with the gold particles. The labeling is even, and is over all OMVs, not restricted to just a fraction of the OMVs. Thus, while half the OMVs in the mixture originally contained no PorA, after blending all OMVs stain positively for PorA, indicating all OMVs now contain PorA.

Thus, the invention provides vesicle-containing, especially OMV-based, preparations and methods for their production.

The invention claimed is:

1. A composition comprising outer membrane vesicles (OMVs) isolated from a first species of *Neisseria* and at least a second species of *Neisseria*, wherein the first species is *Neisseria meningitidis* and the at least second species is a commensal *Neisseria*.

2. The composition of claim 1, further comprising a pharmaceutically acceptable carrier.

3. The composition of claim 1, wherein either or both of said first and said at least second *Neisseria* species comprises a heterologous antigen.

4. A blended OMV composition consisting essentially of outer membrane vesicles (OMVs) extracted from *Neisseria lactamica* and OMVs extracted from *Neisseria meningitidis*.

* * * * *